US005266492A

United States Patent [19]

Wood et al.

[11] Patent Number: 5,266,492

[45] Date of Patent: Nov. 30, 1993

[54] RAPID METHOD FOR DETERMINING CRITICAL VAPOR PRESSURE

[75] Inventors: Ray W. Wood, Elkhorn, Wis.; Lee D. Hansen, Orem; John W. Crawford, Salem, both of Utah

[73] Assignee: Baxter International Inc., Deerfield, Ill.

[21] Appl. No.: 975,641

[22] Filed: Nov. 13, 1992

[51] Int. Cl.[5] ........................ G01N 7/16; G01N 25/20

[52] U.S. Cl. ........................................ 436/34; 422/51; 422/68.1; 422/82.12; 422/82.13; 436/39; 436/147; 436/148; 436/157

[58] Field of Search ................... 436/34, 39, 147, 148, 436/157; 422/51, 68.1, 82.12, 82.13

[56] References Cited

U.S. PATENT DOCUMENTS 3,833,340 9/1974 Jones et al. ..................... 436/147 X

OTHER PUBLICATIONS

Strickland, W. A., Jr., "Study Of Water Vapor Sorption By Pharmaceutical Powders," *Journal of Pharmaceutical Sciences*, vol. 51, No. 4, 1962, pp. 310-314.

Michniak-Mikolajczak, B. B., et al., "A Microbalance Technique For Measuring Water Vapour Uptake And Release By Stratum Corneum In Vitro," *International Journal of Pharmaceutics*, vol. 31, 1986, pp. 247-259.

*Primary Examiner*—Jill A. Johnston
*Attorney, Agent, or Firm*—Amy L. H. Rockwell; Paul E. Schaafsma; Paul C. Flattery

[57] ABSTRACT

A method of determining the critical vapor pressure of a hygroscopic material, such as a drug. A drug sample is placed in a substantially isothermal environment. A vapor, such as water vapor, at a given pressure is then placed in the ambient air over the drug. The rate of heat production from this sample at the given water vapor pressure, or the humidity of the air above the sample, is then measured. The water vapor pressure over the drug is gradually increased. Simultaneously, the rate of increase in heat production from the drug sample, or the rate of change of the relative humidity of the air above the drug sample, is measured. A marked increase in the rate of heat production generated by the drug, or a marked change in the relative humidity of the air over the sample, signals the attainment of the critical water vapor pressure.

21 Claims, 8 Drawing Sheets

RAPID METHOD FOR DETERMINING CRITICAL VAPOR PRESSURE

DESCRIPTION

1. Technical Field

This invention relates to a method of determining the critical vapor pressure of a substance. Particularly, this invention relates to a rapid method of determining the critical water vapor pressure of a drug. In this way, drug manufacturers may package or store that drug in an environment designed to ensure that the critical water vapor pressure will not be reached.

2. Background of the Invention

Many hygroscopic materials, such as pharmaceuticals, superabsorbents, plant tissues, polymers and agricultural chemicals, may be harmed through contact with atmospheric moisture. In the case of pharmaceuticals, both the nonactive excipients and the active drugs are subject to physical property change, degradation or phase change when exposed to adverse, relatively high moisture environments. Thus, pharmaceutical manufacturers must know the conditions under which each particular pharmaceutical will and will not degrade. Knowing these conditions, manufacturers can use the least expensive packaging materials available that are able to ensure that such adverse conditions will not occur.

For example, a particular inexpensive foil seal for a bottle opening may have a known permeability. That permeability may be sufficiently low to ensure that environmental moisture could not increase the water vapor pressure in that bottle to a level near or above the critical water vapor pressure of a given drug. In such a case, the manufacturer would be confident in using this foil seal, rather than a more expensive seal having a lower permeability.

Currently, the critical water vapor pressure of pharmaceuticals is measured by time-consuming methods. Typically, these methods require weeks or months to complete. Examples of currently used methods for determining the critical water vapor pressure are described in W. A. Strickland, Jr., "Study Of Water Vapor Sorption By Pharmaceutical Powders," *J. Pharmaceutical Sciences,* 51, (1962) 310–314, and in B. B. Michniak-Mikolajczak, B. W. Barry and L. L. Walker, "A Microbalance Technique For Measuring Water Vapour Uptake And Release By Stratum Corneum In Vitro," *International J. of Pharmaceutics,* 31, (1986) 247–259.

In the case of agricultural chemicals, such as fertilizers, exceeding the critical water vapor pressure can result in a conversion of that fertilizer from a granular, free-flowing substance to a caked, agglomerated substance. This causes obvious difficulties in handling and application of the fertilizer.

SUMMARY OF THE INVENTION

The invention is a method of determining the critical vapor pressure of a drug or any other hygroscopic material, including, but not limited to, agricultural chemicals such as fertilizers. In accordance with one aspect of this method, a drug sample may be placed in a substantially isothermal environment. Water vapor at a given pressure is then placed in the ambient air over the drug. The rate of heat production from this sample at that given water vapor pressure is then measured. The water vapor pressure over the drug is gradually increased by a method called "scanning." Scanning is the continual, upward variance in the water vapor pressure in contact with a drug sample by an increase in the temperature of the water which is the source of the vapor pressure. Simultaneously, the rate of heat production from the drug sample is measured. A marked increase in the rate of heat production generated by the drug signals the attainment of the critical water vapor pressure.

A further aspect of the invention is another method of determining the critical water vapor pressure of a drug. This aspect is similar to the first method, but measures changes in water vapor pressure of the ambient air over the drug sample as a signal that the critical water vapor pressure has been attained. In particular, this method comprises placing the drug in an isothermal environment, and then determining the moisture content of the air directly above the sample. The water vapor pressure over the drug is then slowly increased. As this pressure is increased, the rate of increase of the relative humidity or moisture content of the air directly above the sample is measured. A change in the rate of increase in the relative humidity or moisture content of the air above the sample signals the attainment of the critical water vapor pressure. The moisture content of the sample upon attainment of the critical water vapor pressure can also be determined through this same measurement.

This invention has the advantage of providing the critical water vapor pressure of a hygroscopic material in a matter of hours, rather than the weeks or months typically necessary for its determination using prior art methods. The method can determine the critical water vapor pressure with either readily fabricated or readily available, relatively inexpensive equipment.

DETAILED DESCRIPTION OF THE PREFERRED EMBODIMENT

The invention is a method of determining the critical vapor pressure of a drug or any other material that is hygroscopic, i.e., can absorb water. Other hygroscopic materials can include agricultural chemicals, such as fertilizers. The critical water vapor pressure is defined as the water vapor pressure in equilibrium between two phases of a solid material. Phases of solid materials can include, for example, an anhydrous material, a hydrate, or a saturated solution of that solid. Although this method can be performed with various types of apparatus, this specification discloses one suitable apparatus for performing the method.

Figure 1:
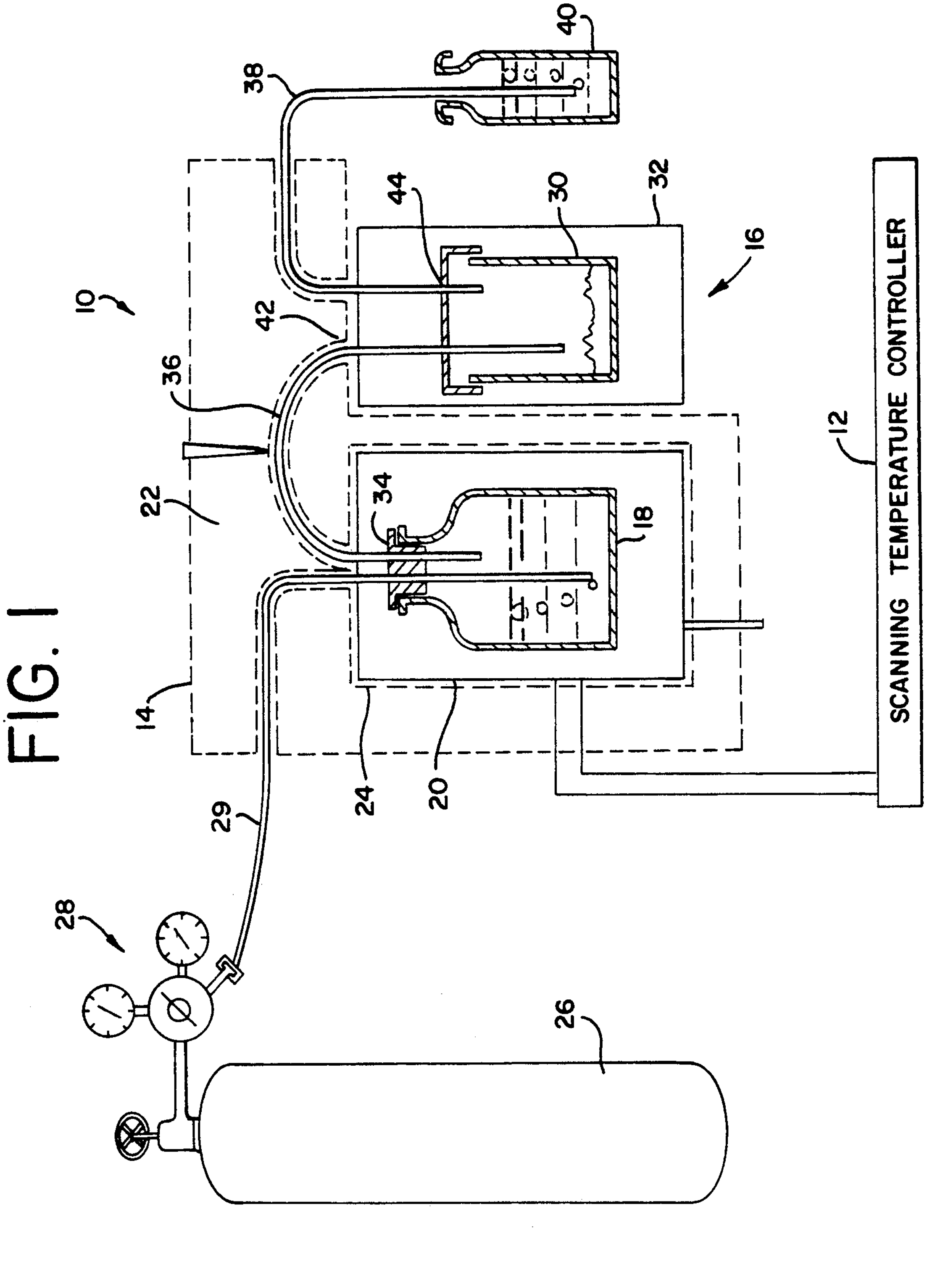
FIG. 1 is a schematic view of an apparatus suitable for use in performing the methods of the invention.

As an overview, FIG. 1 is a schematic diagram of this suitable apparatus 10. It shows the apparatus in principle, and details of the actual appearance of a suitable apparatus may vary, as will be recognized by those skilled in the art. The schematic will be described in the context of the particular apparatus used by the inventors.

There are three main components of this apparatus. They are (1) a scanning temperature controller 12; (2) a temperature scanning block 14; and (3) an isothermal heat flux calorimeter 16.

The schematic diagram of FIG. 1 is intended to represent three bottles 18 within the temperature scanning block. The specially fabricated temperature scanning block 14 is the source of heat for this apparatus. The temperature scanning block 14 provides heat to the system by its contact with a conductive well 20 or housing which is a part of the temperature scanning block and which encloses these bottles 18. A styrofoam enclosure 22, heated by a manually controlled, alternating current power source, surrounds the temperature scanning block 14 to avoid heat losses from the system and prevent condensation in the gas flow lines. The styrofoam enclosure 22 encloses heating element 24, and that heating element 24 is a wafer heater.

Although a three bottle system may be used, one bottle 18 is sufficient to carry out the method of this invention. Accordingly, various portions of the following description and overview of this device will assume the presence of only one bottle 18.

The scanning temperature controller 12 used in this method was built by the inventors. Custom-made scanning temperature controllers are available, for example, from Hart Scientific. The purpose of the scanning temperature controller 12 is to increase the temperature of the temperature scanning block 14 in a gradual, but very precise, manner. For the purposes of this invention, scanning is defined as a gradual, as opposed to stepwise, increase of temperature over time. In this embodiment, the preferred increase in temperature of the scanning block is 1°-7° C. per hour. As a result, the temperature of a bottle 18 enclosed within that temperature scanning block, and the vapor pressure of the water within that bottle, will also increase. The rate of increase of the temperature in the bottle 18 will very closely approximate the rate of increase in the temperature of the temperature scanning block 14. This close approximation between the two rates of increase was established to the satisfaction of the inventors based upon the agreement of the critical water vapor pressures of known drugs, when determined through this method and when compared with published values for those drugs.

As may be seen in FIG. the apparatus includes a nitrogen gas tank 26 that serves as a source of nitrogen gas. A glass capillary 29 having an internal diameter of twenty-five micrometers connects nitrogen gas tank 26, through appropriate pressure regulators 28, to the bottle 18 within the temperature scanning block 14. The glass capillary 29 provides precise control of the gas flow rate. Nitrogen is dispensed into the bottle 18 as a carrier gas, and ensures transfer of the water vapor from the bottle 18 to an ampule 30 within the isothermal heat flux calorimeter 16, as will be explained below. Through this mechanism, the water vapor pressure over the sample in the ampule 30 is gradually increased. Although nitrogen is used in this embodiment, any dry gas that does not react with the sample will also be suitable.

One of the important innovations in this method is the discovery that precise control of the gas flow rate from the nitrogen gas tank 26 is essential. The flow rate of nitrogen depends on the upstream pressure, and on the length and internal diameter of the capillary. For example, capillary 29, having a length of 3 feet and an internal diameter of 25 micrometers insures precision in the delivery of the nitrogen to the bottle 18. Although accuracy is desirable, precision in the rate of the nitrogen gas flow is far more important. In other words, it is necessary that there be consistent gas flow delivery throughout the time that the method is being performed.

The scanning temperature controller 12 is positioned between a conventional, 110 V. alternating current (AC) power source and the temperature scanning block 14. The scanning temperature controller 12 controls the temperature of the temperature scanning block 14.

A glass capillary 36 connects the bottle 18 in the well to sample ampule 30 in a cell 32 within the isothermal heat flux calorimeter 16. The ampule 30, in turn, contains a small, typically 50 mg sample of the drug to be tested. Increases in heat output by the drug sample are transferred to the ampule 30, then to cell 32, and the increases are then measured by the isothermal heat flux calorimeter 16 that encloses the ampule and cell. Particularly, the isothermal heat flux calorimeter 16 containing this ampule measures the rate of heat production by the drug as the water vapor pressure over that drug is slowly increased. When the rate of heat production generated by the drug increases markedly, this signals that the drug has become hygroscopic, and further signals attainment of the critical water vapor pressure. The critical water vapor pressure is signalled by a change in the rate of water uptake, which can be determined calorimetrically.

In this specification, the method is described in terms of the use of water vapor and critical water vapor pressures. It should be understood by those in the art that other kinds of vapors can be used to perform the present method. For example, a volatile alcohol could be used in lieu of water. Phase change of the solid could then be described in terms of a critical alcohol vapor pressure.

Reviewing the apparatus of FIG. 1 in more detail, the temperature scanning block 14 is constructed from aluminum. The temperature scanning block 14 is essentially a 3 inch cube having up to four wells 20. Each of these four wells 20 holds a glass or plastic bottle 18 with about 30 milliliters of water. The temperature of this block 14 is measured with a thermocouple or, preferably, a semiconductor temperature sensor. An IBM XT computer is programmed to collect data for the temperature scanning block 14.

The temperature scanning block 14 is mounted on the chassis of the isothermal heat flux calorimeter 16, such as a Hart Scientific Model No. 7707 differential scanning calorimeter. The styrofoam enclosure 22 surrounds both the temperature scanning block 14 and an opening into the isothermal heat flux calorimeter 16. This styrofoam enclosure 22 is comprised of 2 inch styrofoam walls, including an upper wall that acts as a box lid. A box heater is placed on the inside of this box lid, and heats the air within the box to a temperature above that of the temperature scanning block 14. The heated air, in turn, prevents the condensation of the water vapor in the gas flow lines between the bottles 18 and the drug-containing ampules 30. The box heater is manually controlled with a Variac controller.

The isothermal heat flux calorimeter 16 has four 1 milliliter sample chambers having removable ampules 30. In this study, all four ampules 30 were used. Two of the ampules were empty. No nitrogen gas flowed into the first of these empty ampules, which acted as an instrument reference. Nitrogen gas flowed to the second of these empty ampules which served as a baseline reference. If no baseline data was required, however, then a drug sample could also be placed into this second empty ampule for testing. Each of the third and fourth ampules contained approximately 50 milligrams of the drug to be tested.

The pressure and flow of the nitrogen in the nitrogen tank 26 is regulated by a two stage pressure regulator 28 having a 400 psig second stage. The nitrogen gas is fed to each of the bottles 18 through glass capillary 29, each capillary 29 being approximately 3 feet long and having an internal diameter of 25 micrometers. Each of the bottles include a serum cap 34 for stoppering and providing the gas lines with access to the bottle 18. With the pressure regulator 28 set at about 80 psig outlet pressure, nitrogen will flow to each of the bottles 18 at a constant rate of approximately 1 milliliter per minute.

Approximately 10–15 milliliters of water is placed into these 30 milliliter capacity bottles 18. A 0.1 cubic centimeter spray trap is also provided.

A second glass capillary 36 for each bottle is provided. This capillary 36 is contained in the insulating, styrofoam box 22, and has a length of approximately 25 centimeters and an internal diameter of 0.1 millimeters. Each capillary 36 connects the spray trap on the outlet of each bottle 18 with an inlet of a corresponding ampule 30, and provides for transfer of water vapor from the bottle to the ampule.

A third glass capillary 38, also having a length of approximately 25 centimeters and an internal diameter of 0.1 millimeters, serves as the outlet from the ampule. This third glass capillary 38 terminates in an open vial 40 of water to provide a visual indication of gas flow.

The testing is started by setting the proper temperature of the sample in the calorimeter 16, i.e., the isothermal sample temperature. The calorimeter 16 is provided with a circulating fluid as part of the temperature control system, and the temperature of this circulating fluid is set 10° C. above the starting temperature. Setting the temperature of the circulating fluid 10° C. above the starting or calorimeter temperature aids in preventing condensation of water in the gas flow lines 36 between the water bottles and the calorimeter ampules 30. Particularly, operating the circulating fluid above the calorimeter temperature ensures that the isothermal shields around the calorimeter are at a higher temperature than the calorimeter. Accordingly, no condensation will occur when the gas flow tubes pass through these shields.

The temperature scanning block 14 is then cooled to the starting temperature. Fifty milligrams of the sample, or approximately enough sample to cover the bottom of the ampule 30, is weighed into the ampule, and the ampules are placed into the calorimeter 16.

Gas flow through the system is started, and the appropriate current to the box heater is provided. One should now wait approximately 30 minutes so that the calorimeter 16 will stabilize.

The IBM XT computer is now programmed to scan the block temperature and collect heat rate data from the calorimeter. The scan rate, or the increase in the block temperature over time, may range from between 1°–7° C. per hour. At scan rates above 10° C. per hour, the endpoint would not appear until after attainment of the actual critical water vapor pressure. This is because either the temperature of the water in the bottles may lag behind the block temperature, or because the reaction rate is limited by the transport rate of the water vapor to the sample. A computer data set consists of (1) the calorimeter temperature, a single number precise to 0.001° C., and accurate to about 0.2 degrees Kelvin; (2) block temperatures collected at a rate of one per minute, precise to 0.001° C. and accurate to about 2° C. in reflecting the water temperature in the bottles in the wells; and (3) sample heat rates matching the block temperatures in time.

Fifty milligrams of the drug to be tested are placed into an ampule 30, and that ampule 30 is, in turn, placed into the isothermal heat flux calorimeter 16. The flow of nitrogen is then commenced through the capillary 29 connecting the nitrogen tank 26 and the bottle 18. Another capillary 36, having an internal diameter of 0.1 mm, serves as a nitrogen gas transfer line between the bottle 18 and the ampule 30. As the nitrogen gas is carried from the bottle 18 to the ampule 30, the water vapor from the bottle is carried with that gas. The temperature of the bottle, and thus the vapor pressure of the water within that bottle, is steadily increasing with the increase in the temperature of that water. As a result, the vapor pressure of the water vapor being carried by the nitrogen to the ampule is steadily increasing, and the vapor pressure over the drug sample steadily increases.

Flow indicator or vial 40 monitors the flow rate of nitrogen, providing visual proof of a continuous flow.

Two steps are necessary in analyzing the data generated. First, the block temperatures are converted to corresponding water vapor pressures using data obtained from the literature, such as "Vapor Pressure Of Water Below 100° C.," *Handbook of Chemistry and Physics,* R. C. Weast (ed.), 55th edition, CRC Press, Cleveland, Ohio, 1974, p. D159. Second, a plot of heat rate (vertical axis) versus the water vapor pressure is constructed.

In reviewing plots of heat rate versus water vapor pressure, the graph typically includes two relatively straight, but differently angled, branches. The first branch is relatively flat, and depicts the slow sorption of water by the drug at pressures below the critical water vapor pressure. The second branch is more steeply angled, and depicts the rapid sorption of water by the drug at the critical water vapor pressure and at pressures above the critical water vapor pressure.

At the critical water vapor pressure, there should theoretically be an immediate transition from the first to the second branch. This immediate transition does not occur, however, and there is instead a gradual change from the first to the second branch. Nevertheless, the critical water vapor pressure can be found by extrapolation of the first and second branches. The critical water vapor pressure is the water vapor pressure at the intersection of these extrapolated branches. The curved portion contains information on the mechanism of water sorption by the drug.

The method was tested by using one compound whose critical water vapor pressure was known. The method was then tested by using six compounds with unknown critical water vapor pressures. The "known" compound was sodium ampicillin. The "unknown" compounds were nafcillin sodium, ceftriaxone sodium, cefazolin sodium, piperacillin sodium, ceftoxime sodium, and cefuroxime. The tests on most compounds were run at four different temperatures, i.e., 24°, 34°, 44° and 54° C. This was done because the critical water vapor pressure for a given compound varies with the temperature of the compound that is being tested.

The results obtained are shown in the following Tables and Figures. Table 1 shows the results of the critical water vapor pressure testing for the single "known" and six "unknown" compounds. The critical water vapor pressures for ampicillin determined by the present method at four different temperatures are listed on the first data-containing line of this Table. Immediately below these entries are the critical water vapor pressures for sodium ampicillin at approximately these same four temperatures as determined by a method published in a paper by one of the co-inventors of the present invention. This paper is entitled "Solid State Stability Of Sodium Ampicillin In The Presence Of Excess Moisture," *Pharmaceutical Research,* supplemental volume, page S-74, 1988. As can be seen from a comparison of the first and second data lines of this Table 1, the results agree quite closely. This agreement demonstrates the acceptability of the present method for determining the critical water vapor pressure of a drug, such as sodium ampicillin.

TABLE 1

| Compounds | Critical Water Vapor Pressures $P^c_{H2O}$ mm Hg at 24.1° C. | $P^c_{H2O}$ mm Hg at 34.1° C. | $P^c_{H2O}$ mm Hg at 44.1° C. | $P^c_{H2O}$ mm Hg at 54.1° C. | van't Hoff ΔH° kJ/mol |
|---|---|---|---|---|---|
| Ampicillin | 15.3 ± 0.2(2)[a] | 23 ± 0(2) | 38 ± 1(2) | 63 ± 2(4) | 38.3 |
| | 12.8(25°) | >23(35°) | >37(45°) | >57(°55) | <40.3 |
| Nafcillin | 13.8 ± 0.6(2) | 24(1) | No[b] | 46 ± 1(3) | 33.6 |
| | 18.7 ± 0.3(2) | 29(1) | 49 ± 1(2) | 72 ± 1(3) | 37.0 |
| Ceftriaxone | 18.5 ± 1.0(3) | 33 ± 2(2) | 43(1) | 50(2) | 26.5 |
| Piperacillin | <15 | <15 | <20 | <20 | — |
| Cefuroxime | NR[c] | NR | NR | NR | — |
| Cefotaxime | 16 ± 1(3) | 37 ± 0(2) | NR | NR | 63.7 |
| Cefazoline | <12 | 23(1) | 35 ± 3(3) | 55(1) | 36.4 |
| $p^{H2O}{}_{mm}$[d] | 22.5 | 40.0 | 68.5 | 113 | 44.01[e] |

[a]Error limits are given as the standard deviation with the number of observations in parentheses.
[b]Not observed.
[c]No reaction.
[d]CRC, reference at middle of page 14 of application.
[e]D. D. Wagman et al., Journal of Phys. and Chem. Reference Data, Vol. 11, 1982, Supplement No. 2.

Figure 2:
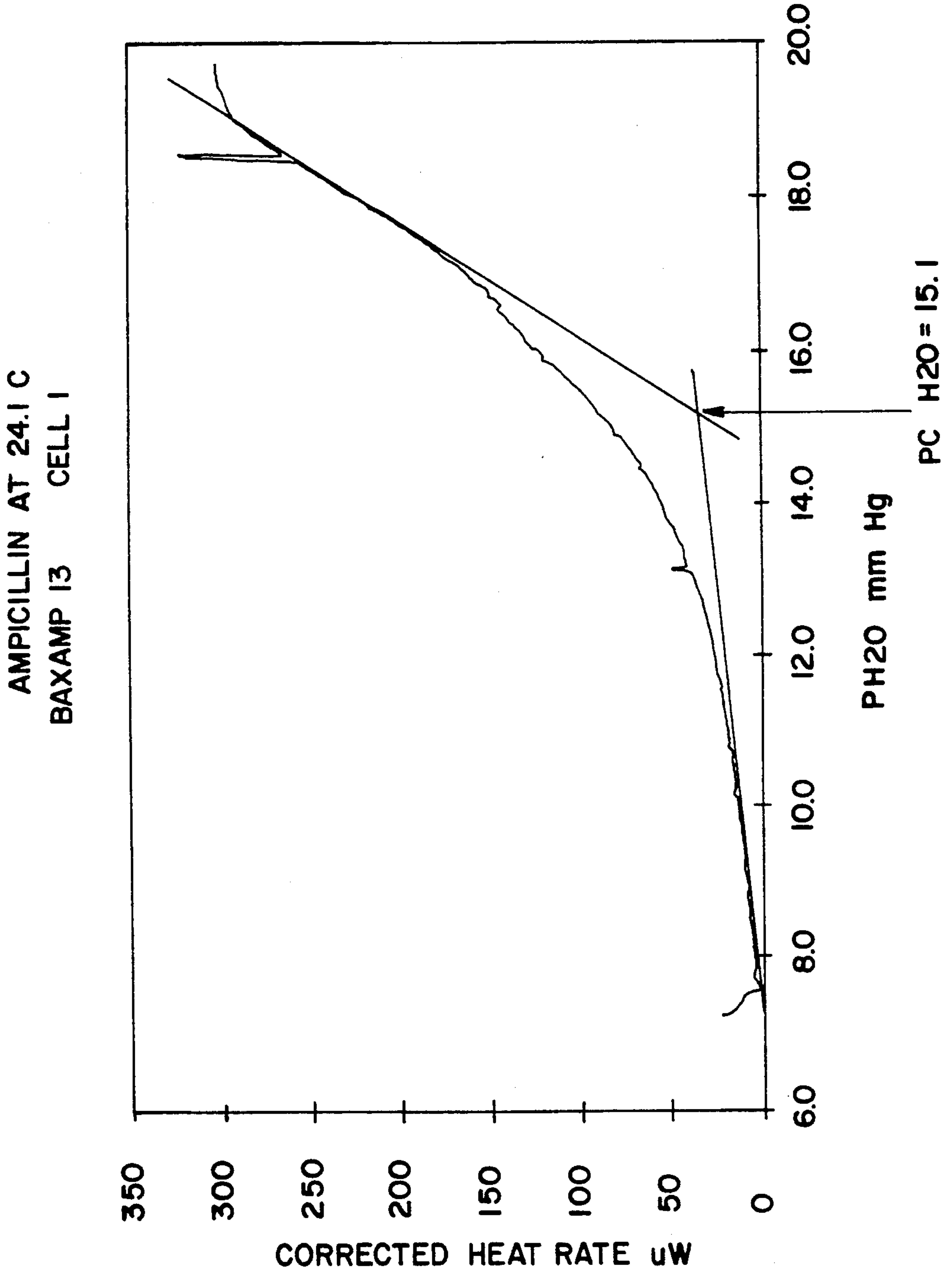
FIG. 2 is a graph of heat output of ampicillin during testing at 24° C. versus water vapor pressure, in mm Hg.
Figure 4:
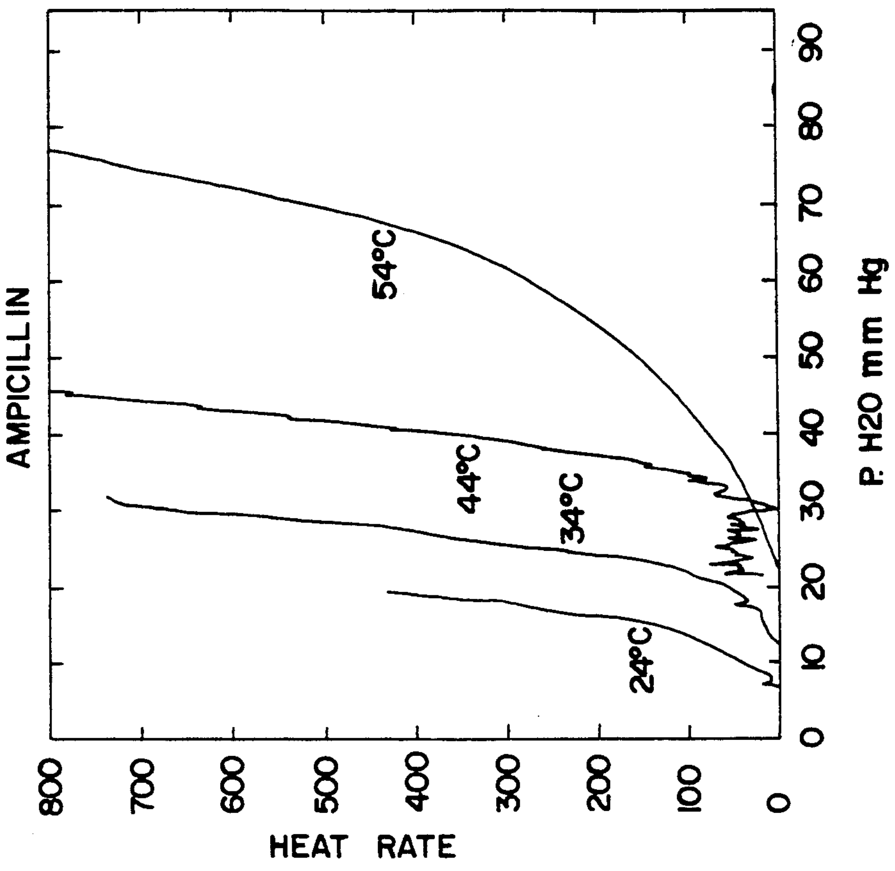
FIG. 4 is a graph of heat output of ampicillin during testing at temperatures of 24°, 34°, 44° and 54° C. versus water vapor pressure, in mm Hg.
Figure 3:
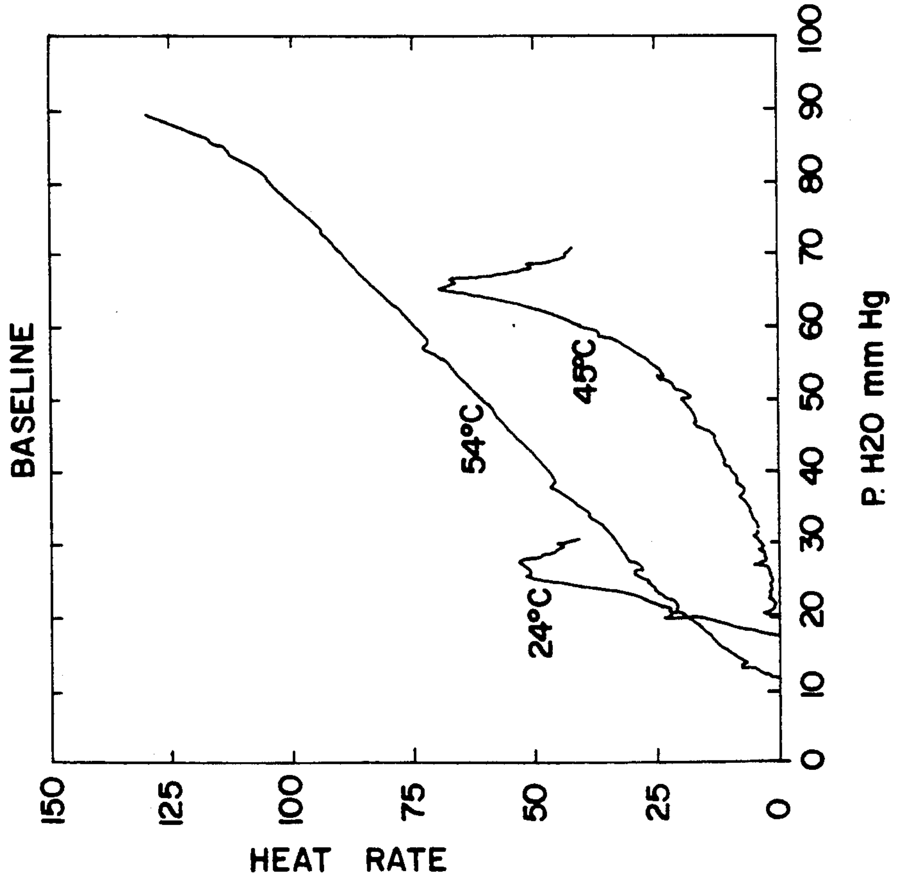
FIG. 3 is a graph of the baseline correction necessary for ampicillin at temperatures of 24°, 45° and 54° C.
Figure 6:
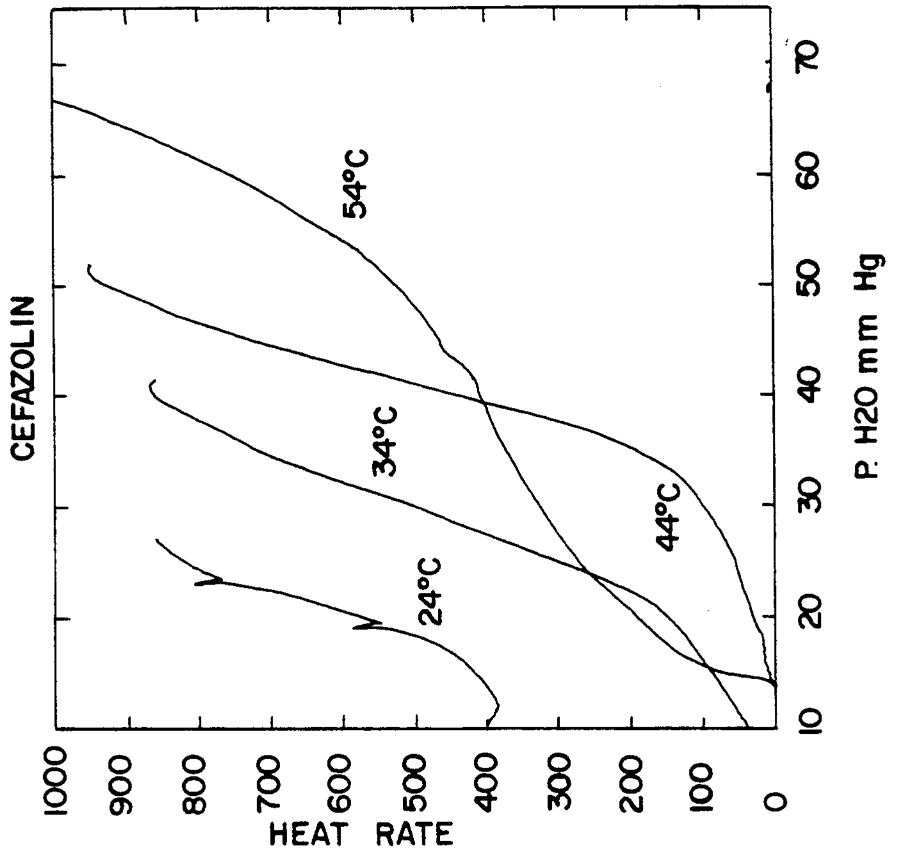
FIG. 6 is a graph of heat output of cefazolin during testing at temperatures of 24°, 34°, 44° and 54° C. versus water vapor pressure, in mm Hg.
Figure 5:
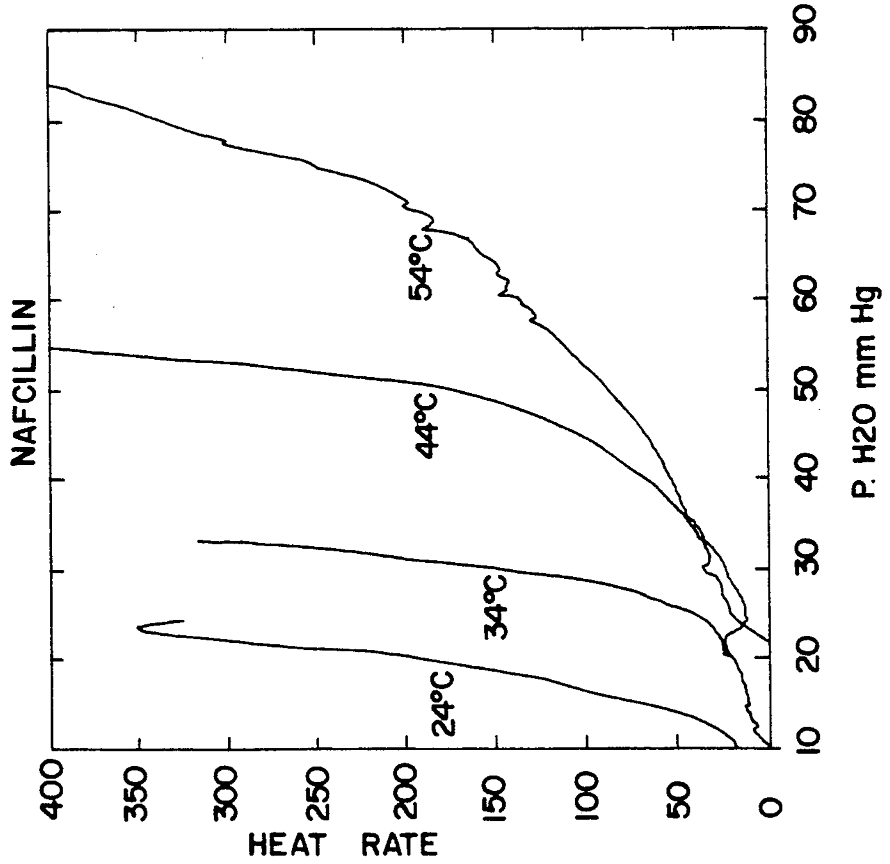
FIG. 5 is a graph of heat output of nafcillin during testing at temperatures of 24°, 34°, 44° and 54° C. versus water vapor pressure, in mm Hg.
Figure 8:
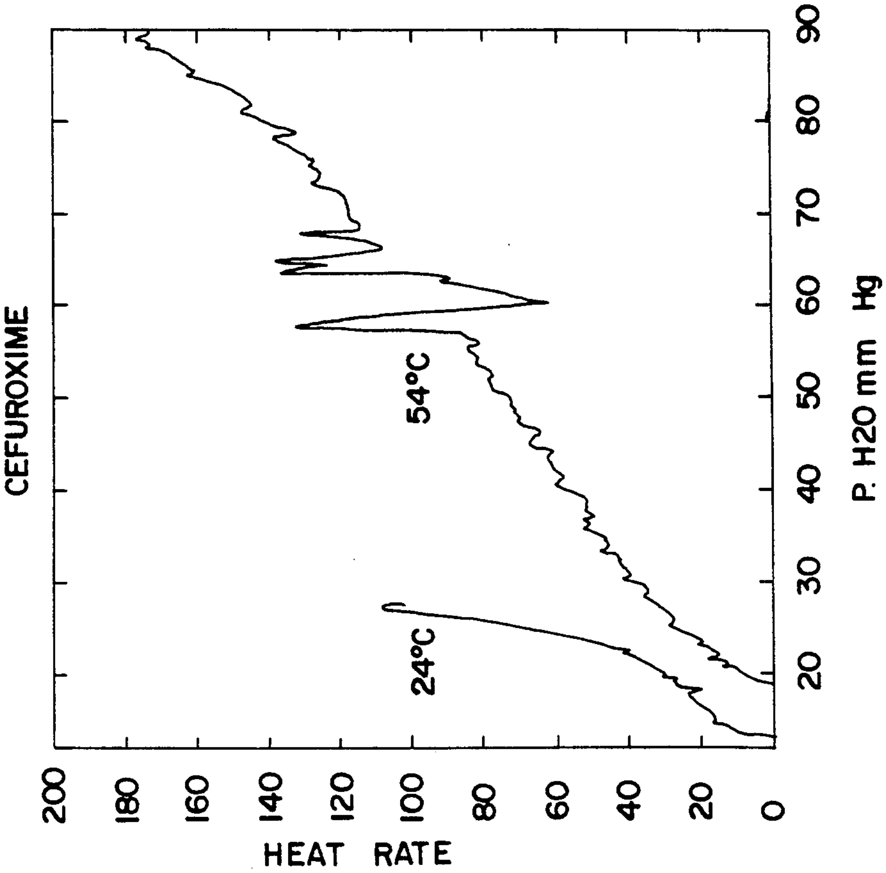
FIG. 8 is a graph of heat output of cefuroxime during testing at temperatures of 24° and 54° C. versus water vapor pressure, in mm Hg.
Figure 7:
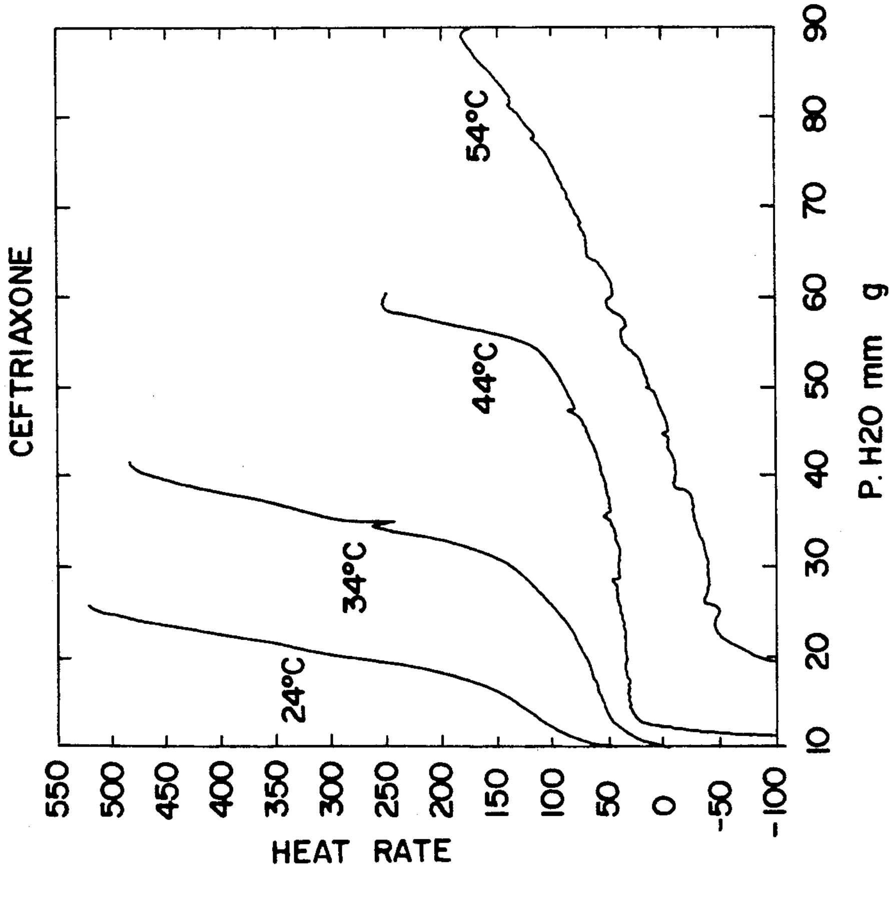
FIG. 7 is a graph of heat output of ceftriaxone during testing at temperatures of 24°, 34°, 44° and 54° C. versus water vapor pressure, in mm Hg.
Figure 10:
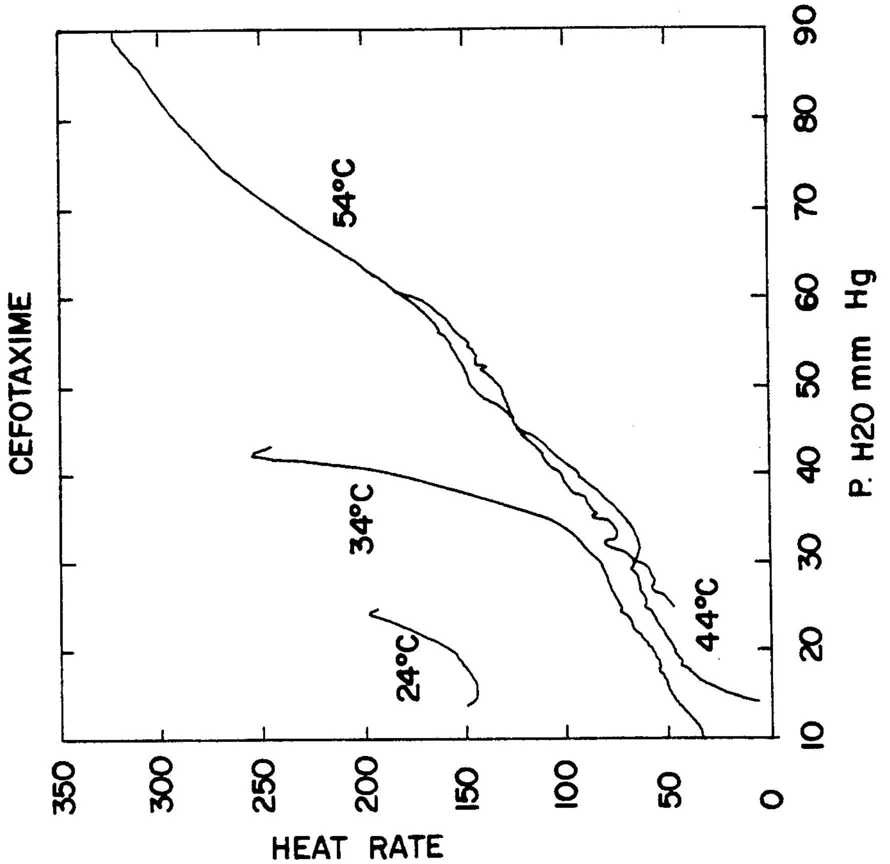
FIG. 10 is a graph of heat output of cefotaxime during testing at temperatures of 24°, 34°, 44° and 54° C. versus water vapor pressure, in mm Hg.
Figure 9:
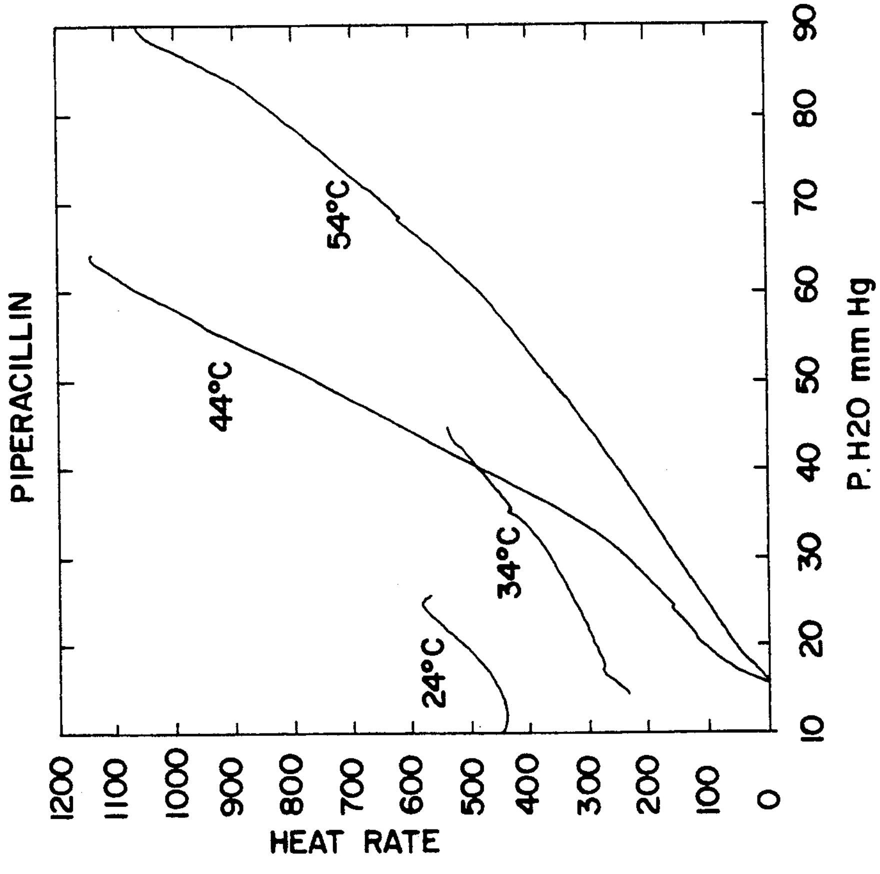
FIG. 9 is a graph of heat output of piperacillin during testing at temperatures of 24°, 34°, 44° and 54° C. versus water vapor pressure, in mm Hg.

FIGS. 2-10 show the plots of heat rates from samples tested versus water vapor pressure for the drugs tested using this method. FIG. 2 shows how this plot is used to extrapolate the first and second branches of the curve to attain, at their intersection, the critical water vapor pressure. This same method was used to determine the critical water vapor pressures for the compounds shown in FIGS. 3-10.

Figure 12:
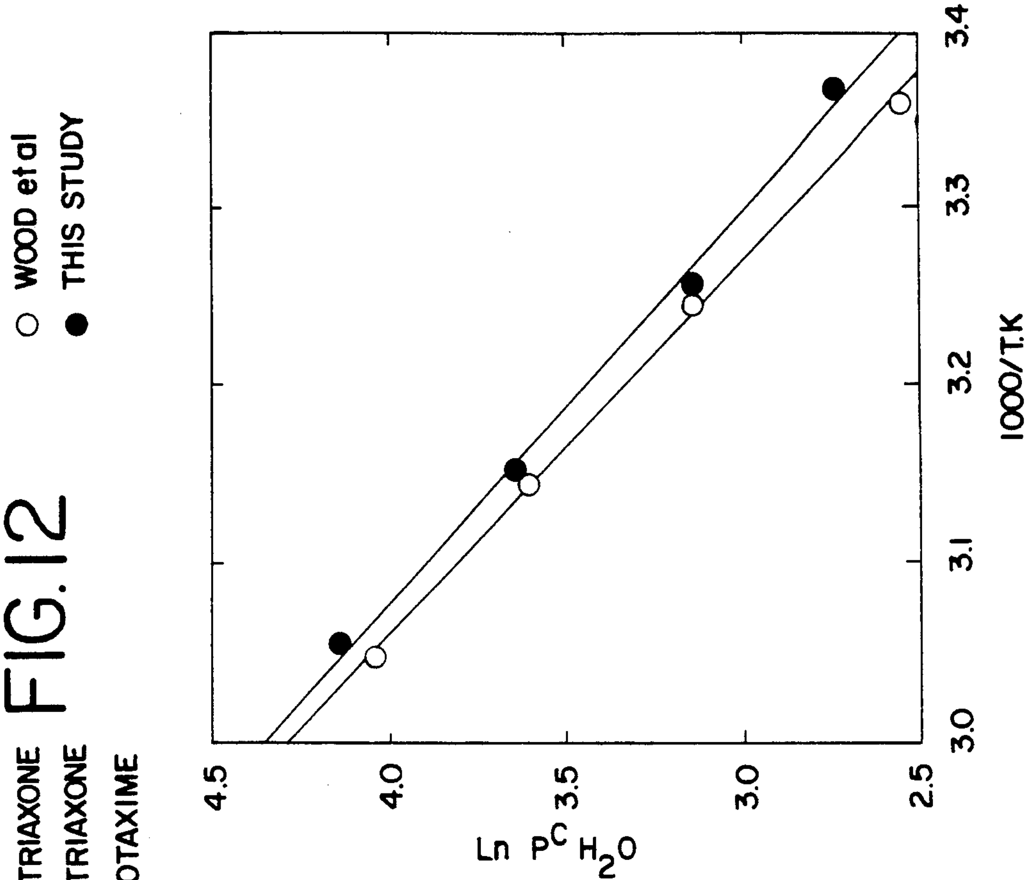
FIG. 12 shows the linear relationship between the natural logarithm of the critical water vapor pressure of ampicillin versus the ratio of 1000 to the temperature, in degrees Kelvin, corresponding to that critical water vapor pressure.
Figure 11:
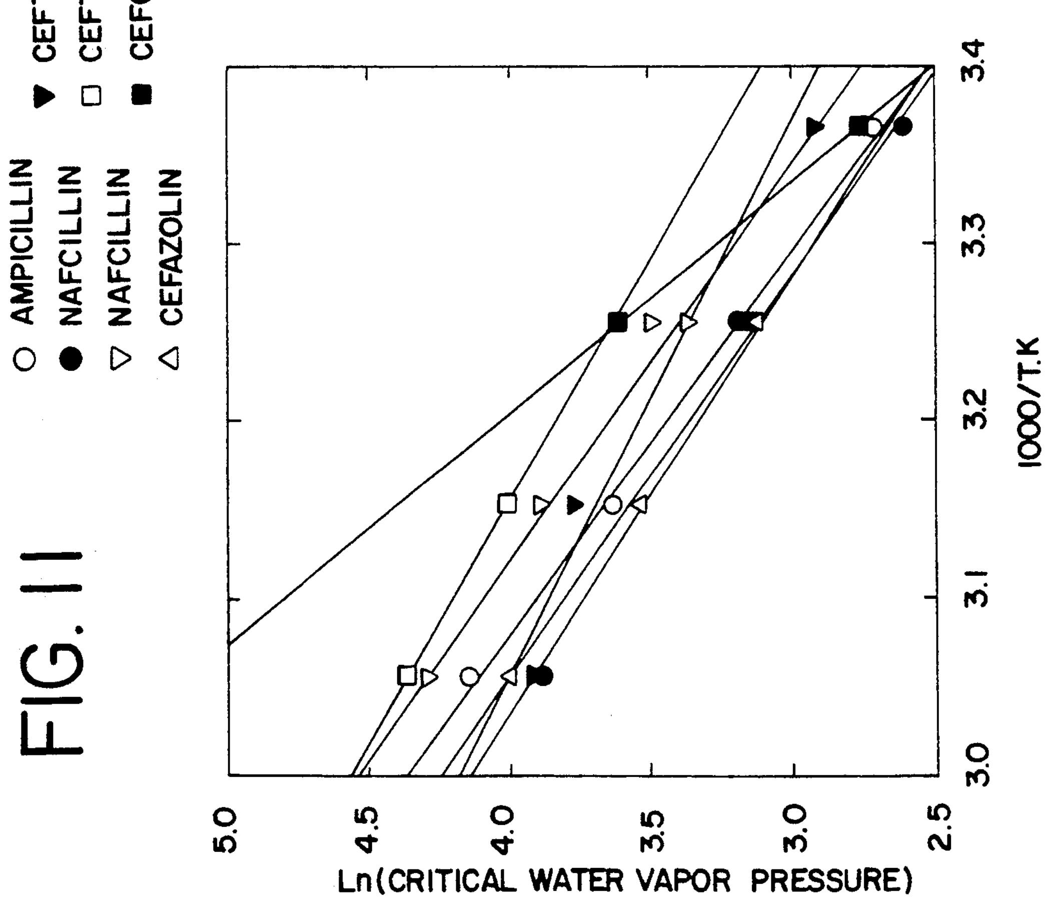
FIG. 11 shows the linear relationship between the natural logarithm of the critical water vapor pressure of five tested drugs versus the ratio of 1000 to the temperature, in degrees Kelvin, corresponding to that critical water vapor pressure.

FIGS. 11 and 12 show the straight line relationship between the natural logarithm of the critical water vapor pressure of a drug at the testing temperature, and the ratio of 1000 to the temperature, in degrees Kelvin, at which the drug is being tested. By interpolation between the data points, one may find the critical water vapor pressure for a given drug at any temperature between 24°-54° C. FIG. 12 compares the straight line established using the results of the tests described in this specification with the line established using the results of the tests from the publication, "Solid State Stability Of Sodium Ampicillin In The Presence Of Excess Moisture," *Pharmaceutical Research,* supplemental volume, page S-74, 1988.

Figure 13:
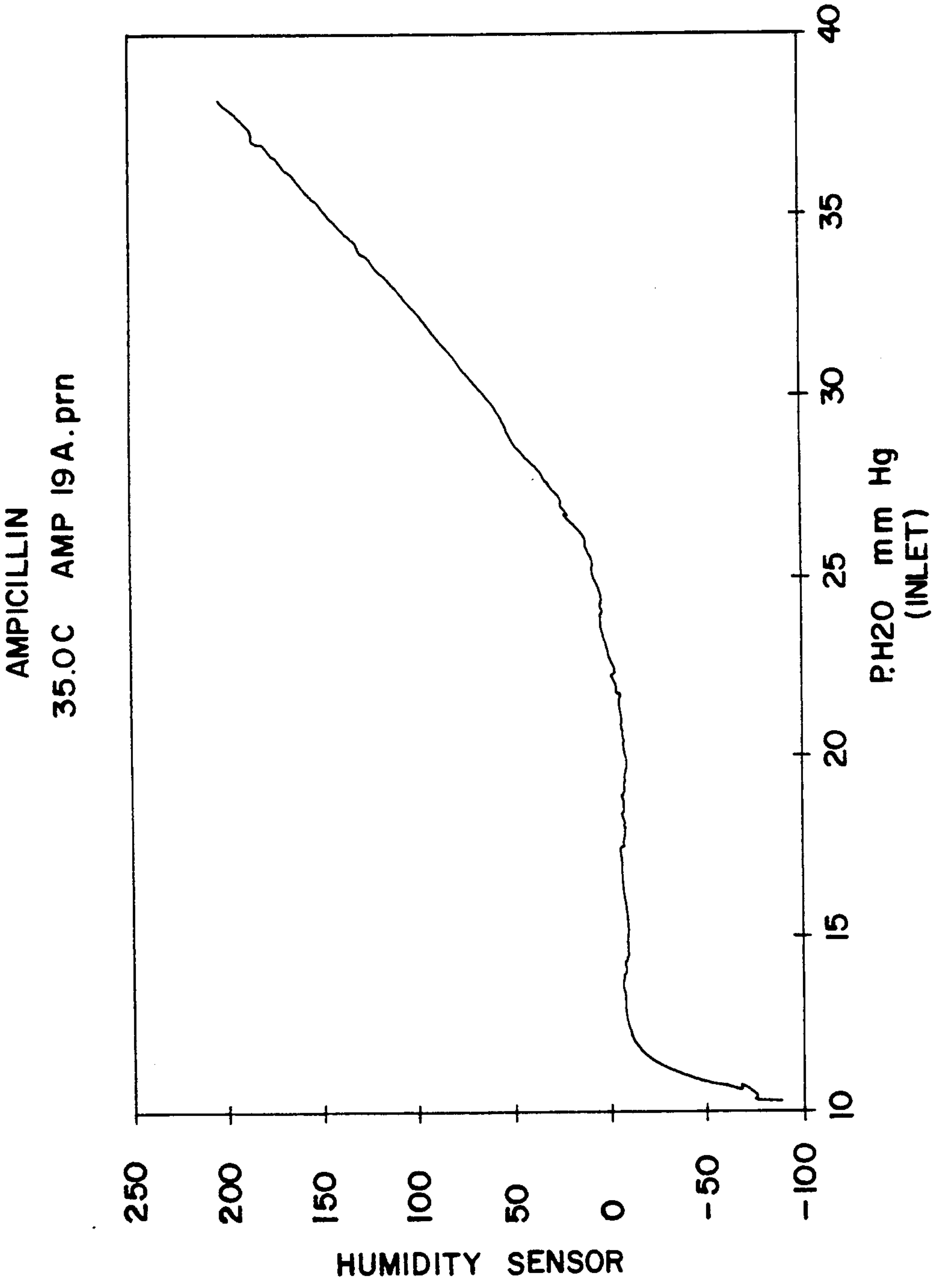
FIG. 13 shows the change in the output of the humidity sensors between the inlet and outlets to an ampule containing ampicillin versus water vapor pressure over ampicillin at 35° C. in an apparatus in accordance with the present invention.

An alternate method of determining the critical water vapor pressure comprises providing the apparatus shown in FIG. 1 with a pair of relative humidity sensors 42 and 44. Particularly, these relative humidity sensors 42 and 44 may be placed at the inlet and outlets, respectively, of an ampule or any other suitable container having a discrete inlet and outlet. The results of a test using this method are shown in FIG. 13. The abscissa of FIG. 13 shows the change in the output of the humidity sensors between the inlet and outlets to the ampule 30 or other container.

As a result of the water vapor pressure within the ampule 30, the drug in the ampule absorbs water and changes phases. As the water vapor pressure of the air in the ampule increases, the water absorbed by the drug will also increase. This increase in water absorbed by the drug is gradual and relatively linear until the attainment of the critical water vapor pressure. When the critical water vapor pressure is reached, the rate of water sorption by the drug increases suddenly and rapidly. As a result, there is no further change in the relative humidity of the air in the ampule and immediately above the drug. Because the air immediately above the drug is removed from the ampule through the ampule outlet, this sudden change in the rate of increase of the humidity is quickly reflected in the signal from the humidity sensor at the outlet of the ampule. Thus, the critical water vapor pressure is signalled by a sudden and marked change in the slope of the line graphing [output minus input ampule water vapor pressure] versus water vapor pressure at the inlet.

By using this second alternate method, one can also determine the increase in moisture content of the hygroscopic material, such as a drug, being tested at the critical water vapor pressure. This can be calculated because the gas flow rate and difference between output and input relative humidity to the sample in the ampule are known. If the carrier gas flow rate is slow enough to allow equilibrium between the sample and water vapor to be reached, the amount of water sorbed by the sample can be calculated. The molecules of water in the water vapor over the drug sample, both before and after attainment of the critical water vapor pressure, can be determined. The difference in the number of water molecules over the drug sample is equal to the number of water molecules adsorbed by the drug sample upon attainment of the critical water vapor pressure. This number of water molecules can be converted into an amount of water in milligrams. This water weight can, in turn, be used to determine the increase in moisture content, by weight, of the drug sample.

Referring to FIG. 13, the intersection of the two main branches of the curve will establish the critical water vapor pressure of ampicillin at 35° C. That intersection is at approximately 26 mm Hg, which is quite close to the value at Table 1. Particularly, the critical water vapor pressure for ampicillin at 34° C., as shown in Table 1, is 23 mm Hg. Thus, the relative humidity method provides yet another rapid method of determining critical water vapor pressure, requiring hours rather than weeks or months.

The inventors have discovered a third alternate method of determining the critical water vapor pressure of a hygroscopic compound. This third method comprises setting a constant temperature (T) with the scanning temperature controller 12 or other type temperature controller. The temperature controller 12 establishes the temperature and, thus, the vapor pressure of the water or other liquid. As a result, there will be a constant water vapor or other vapor pressure in the gas that will flow through the tube 36 and into contact with the hygroscopic material in ampule 30.

Prior to commencing the gas flow, a temperature higher than temperature T is set in calorimeter 16. Approximately 30 minutes is allowed for the temperature of the calorimeter to stabilize and for the hygroscopic material in ampule 30 to reach the calorimeter temperature. The gas flow is then started so that the water vapor flows through tube 36 into the ampule 30.

The calorimeter temperature, which is virtually identical to the temperature of the hygroscopic material in that calorimeter, is then scanned downwardly at a rate of 1°-7° C. per hour until the calorimeter temperature reaches the temperature T. During the scanning process, a record is kept of the calorimeter output. This calorimeter output corresponds to the heat output from the hygroscopic material.

A plot is then made of the calorimeter/hygroscopic material heat output (abcissa) versus the calorimeter, and hygroscopic material, temperature (ordinate). The slopes of the resulting curve are similar to the slopes of the curves of FIGS. 2-10. As with FIG. 2, the extrapolated intersection of the two main branches of the curve will establish a sought-after after value. In the case of this plot, that value will be the temperature, Tc, at which the vapor pressure of water through tube 36 equals the critical water vapor pressure of the sample of hygroscopic material.

This same procedure may be repeated with different values of T to establish a plot similar to that of FIG. 11. The critical water vapor pressure is plotted on the ordinate, as 1000/Tc, where Tc is a temperature in degrees Kelvin. The natural log of vapor pressures at T, i.e., the natural log of the critical water vapor pressure, is plotted on the abcissa. Using such a plot, one may find the critical water vapor pressure at any point on the resulting relatively straight line.

This third method has certain advantages and disadvantages over the first two methods described above. The advantages include the ability to replace the scanning temperature controller 12 with a simple, less expensive, nonscanning temperature controller. Disadvantages include the role of the temperature, rather than the critical water vapor pressure, as the dependent variable. This is less desirable, as preferred storage and use conditions for hygroscopic materials are generally known, while preferred humidity for those materials is not.

While the specific embodiments have been illustrated and described, numerous modifications come to mind without markedly departing from the spirit of the invention. The scope of protection is, thus, only intended to be limited by the scope of the accompanying Claims.

What I claim is:

1. A method of determining the critical vapor pressure of a hygroscopic material, said method comprising:

a. placing said hygroscopic material in an isothermal environment;
b. placing vapor of a given pressure over said hygroscopic material;
c. measuring the rate of heat production from said hygroscopic material;
d. slowly increasing the vapor pressure over said hygroscopic material; and
e. measuring the rate of heat production by said hygroscopic material until the rate of heat production generated by said hygroscopic material increases markedly to signal attainment of the critical vapor pressure of said hygroscopic material.

2. The method of claim 1, wherein said slow increase in the vapor pressure is effected by linear, continuous increases in vapor pressure.

3. The method of claim 1, wherein said slow increase in the vapor pressure is effected by incremental increases in vapor pressure.

4. The method of claim 1, wherein said hygroscopic material is a drug.

5. The method of claim 1, wherein said hygroscopic material is an agricultural fertilizer.

6. The method of determining the critical water vapor pressure of a hygroscopic material, said method comprising:

a. placing said hygroscopic material in a container in an isothermal environment;
b. determining the relative humidity of a gas directly above said hygroscopic material;
c. slowly increasing, in a relatively constant manner, the relative humidity of the gas in the container which contains said hygroscopic material; and
d. measuring the rate of increase of the relative humidity of the gas directly above the hygroscopic material until the rate of increase of the relative humidity of the gas directly above the hygroscopic material changes markedly, said marked change signalling attainment of the critical water vapor pressure of said hygroscopic material.

7. The method of claim 6, wherein said slow increase in the water vapor pressure is effected by linear, continuous increases in water vapor pressure.

8. The method of claim 6, wherein said slow increase in the water vapor pressure is effected by incremental increases in water vapor pressure.

9. The method of claim 6, wherein said hygroscopic material is a drug.

10. The method of claim 6, wherein said hygroscopic material is an agricultural fertilizer.

11. A method of determining the critical vapor pressure of a hygroscopic material, said method comprising:

a. placing said hygroscopic material in a container;

b. placing vapor of given pressure over said hygrosopic material in said container;

c. slowly increasing the vapor pressure over said hygroscopic material; and d. continuously measuring the rate of heat production by said hygroscopic material; until the rate of heat production generated by said hygroscopic material increases markedly to signal attainment of the critical vapor pressure of said hygroscopic material.

12. The method of claim 11, wherein said slow increase in the vapor pressure is effected by linear continuous increases in vapor pressure.

13. The method of claim 11, wherein said slow increase in the vapor pressure is effected by incremental increases in vapor pressure.

14. The method of claim 11, wherein said hygroscopic material is a drug.

15. The method of claim 11, wherein said hygroscopic material is an agricultural fertilizer.

16. A method of determining the critical water vapor pressure of a hygroscopic material, said method comprising:

a. placing said hygroscopic material in a container;

b. slowly increasing, in a relatively constant manner, the relative humidity of a gas in the container which contains said hygroscopic material; and c. measuring the rate of increase of the relative humidity of the gas directly above the hygroscopic material until the rate of increase of the relative humidity of the gas directly above the hygroscopic material changes markedly, said marked change signalling attainment of the critical water vapor pressure of said hygroscopic material.

17. The method of claim 16, wherein said slow increase in the vapor pressure is effected by linear, continuous increases in water vapor pressure.

18. The method of claim 16, wherein said slow increase in the water vapor pressure is effected by incremental increases in water vapor pressure.

19. The method of claim 16, wherein said hygroscopic material is a drug.

20. A method of determining the critical vapor pressure of a hygroscopic material, said method comprising:

a. placing a sample of hygroscopic material in a container;

b. establishing a constant vapor pressure over said hygroscopic material;

c. placing said hygroscopic material at a temperature above a given temperature T;

d. slowly lowering the temperature of the hygroscopic material until the temperature of the hygroscopic material reaches the temperature T;

e. recording the heat output from the hygroscopic material while lowering its temperature; and f. plotting the hygroscopic material heat output versus the hygroscopic material temperature, the intersection of two branches of a resulting curve corresponding to a temperature, Tc, at which the vapor pressure over the hygroscopic material corresponds to the critical vapor pressure of the sample of hygroscopic material.

21. The method of claim 20, wherein the temperature of the hygroscopic material is lowered at a rate of 1°–7° C. per hour.

* * * * *

UNITED STATES PATENT AND TRADEMARK OFFICE

CERTIFICATE OF CORRECTION

PATENT NO. : 5,266,492

DATED : November 30, 1993

INVENTOR(S) : Wood et al.

It is certified that error appears in the above-indentified patent and that said Letters Patent is hereby corrected as shown below:

Column 4, line 13, after "FIG." insert -- 1, --.

Column 10, line 56, Claim 6, before "method" delete "The" and insert --A--.

Signed and Sealed this

Sixteenth Day of August, 1994

*Attest:*

BRUCE LEHMAN

*Attesting Officer*

*Commissioner of Patents and Trademarks*